(12) United States Patent
Carlson et al.

(10) Patent No.: US 8,952,102 B2
(45) Date of Patent: Feb. 10, 2015

(54) ALKYL ETHER COMPOSITIONS AND METHODS OF USE

(71) Applicant: Empire Technology Development LLC, Wilmington, DE (US)

(72) Inventors: William B. Carlson, Seattle, WA (US); Gregory D. Phelan, Cortland, NY (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/297,990

(22) Filed: Jun. 6, 2014

(65) Prior Publication Data

US 2014/0288332 A1   Sep. 25, 2014

Related U.S. Application Data

(63) Continuation of application No. 13/761,512, filed on Feb. 7, 2013, now Pat. No. 8,779,070.

(51) Int. Cl.
| | |
|---|---|
| *C08G 65/32* | (2006.01) |
| *C07C 43/115* | (2006.01) |
| *C07C 43/10* | (2006.01) |
| *C08G 65/00* | (2006.01) |
| *C07C 43/04* | (2006.01) |
| *C08L 71/02* | (2006.01) |

(52) U.S. Cl.
CPC ............... *C07C 43/115* (2013.01); *C07C 43/10* (2013.01); *C08G 65/00* (2013.01); *C08L 71/02* (2013.01); *C07C 43/04* (2013.01)
USPC .......................................................... 525/403

(58) Field of Classification Search
USPC .......................................................... 525/403
See application file for complete search history.

(56) References Cited

U.S. PATENT DOCUMENTS

| | | | |
|---|---|---|---|
| 2,067,465 | A | 1/1937 | Horst |
| 3,098,061 | A | 7/1963 | Heck |
| 5,476,653 | A | 12/1995 | Pitt et al. |
| 2007/0179255 | A1 | 8/2007 | Vedula et al. |

FOREIGN PATENT DOCUMENTS

GB   0 928 159   6/1963

OTHER PUBLICATIONS

Bajwa, Naval et al., "An Efficient 1,2-Chelation-Controlled Reduction of Protected Hydroxy Ketones via Red-Al," J. Org. Chem., 2008, vol. 73, No. 9, pp. 3638-3641.
Berliner, Martin A. et al., "Simple, Rapid Procedure for the Synthesis of Chloromethyl Methyl Ether and Other Chloro Alkyl Ethers," J. Org. Chem., Nov. 2005, 70(23), pp. 9618-9621.
Fujioka, H. et al., "Novel Regiocontrolled Protection of 1,2- and 1,3-Diols via Mild Cleavage of Methylene Acetals," Org. Lett., 2009, 11(22), pp. 5138-5141.
Hitachi, Ltd., (Kazuo Furukawa, President and CEO) "Successful trial of non-volatile RAM Chip 2 megabites using spin injection magnetization switching method," 2007, 3 pages. Retrieved from: http://www.nistep.go.jp/achiev/ftx/jpn/stfc/stt080j/0711_02_topics/200711_topics.html.
International Search Report and Written Opinion received for PCT/US2012/048980 dated Jan. 2, 2013.
Non-Final Office Action in U.S. Appl. No. 13/761,512 dtd Dec. 31, 2013 (5 pages).
Notice of Allowance in U.S. Appl. No. 13/761,512 dtd Mar. 14, 2014 (5 pages).
Ramesh, C. et al., "Simple, Efficient, and Selective Deprotection of Phenolic Methoxymethyl Ethers Using Silica-Supported Sodium Hydrogen Sulfate as a Heterogeneous Catalyst," J. Org. Chem., 2003, 68(18), pp. 7101-7103.
Sato, O. et al., "Chemical Recycling of PET Technology Using Only Water," AIST Today, vol. 6, No. 9, 2006, 5 pages. Retrieved from: http://www.aist.go.jp/aist_j/aistinfo/aist_today/vol06_09/p28.html.

*Primary Examiner* — Terressa Boykin
(74) *Attorney, Agent, or Firm* — Foley & Lardner LLP

(57) ABSTRACT

A polymer includes a linker represented by Formula I ($[OR^1OCH_2OR^2OCH_2]_m$), where $R^1$ and $R^2$ are, independently, alkylene, alkenylene, arylene, heteroarylene, or alkylarylalkylene; and the polymer has a weight average molecular weight of about 500 g/mol to about 2,000,000 g/mol, and m is 1 to 1000.

18 Claims, No Drawings

ALKYL ETHER COMPOSITIONS AND METHODS OF USE

CROSS-REFERENCE TO RELATED APPLICATIONS

This application is a continuation of U.S. patent application Ser. No. 13/761,512, filed on Feb. 7, 2013, which in turn claims the benefit of International Application Serial No. PCT/US2012/048980, filed on Jul. 31, 2012, the entire disclosure of which is hereby incorporated by reference for all purposes in its entirety as if fully set forth herein.

FIELD

The present technology relates to polymers that are degradable and recyclable and plastic materials that are made from such polymers.

BACKGROUND

The following description is provided to assist the understanding of the reader. None of the information provided or references cited is admitted to be prior art to the present technology.

Commercially relevant packaging materials are constantly evolving to meet consumer demand for improved products by combining numerous physical characteristics, such as flexibility, light weight, or strength into such packaging materials. Unfortunately, despite improvements in product performance, most of these commercially relevant packaging materials remain difficult or impractical to recycle. Unless it is biodegradable, the discarded packaging materials accumulate in landfills and waterways, where they may eventually harm ecosystems and wildlife. Consequently, the food packaging industry is seeking packaging materials that satisfy the evolving demands of consumers, yet can be more readily degraded and recycled.

SUMMARY

The present technology provides for a recyclable polymer that includes monomers joined by acid-sensitive —OCH$_2$O— linkers that can be cleaved upon exposure to acidic conditions. The recyclable polymer, having monomers joined by acid-sensitive —OCH$_2$O— linkers, can be incorporated into plastic materials such as, for example, food packaging or consumer packaging materials. After the plastic materials have been used by a consumer they can readily be degraded by subjecting the plastic materials to acidic conditions. Upon treatment with acid, the —OCH$_2$O— linkers within the polymers are hydrolyzed, the monomers are released, and the plastic materials are thus degraded. The resulting monomers can be recombined with additional acid-sensitive —OCH$_2$O— linkers to regenerate the polymer and recycle the plastic materials.

In one aspect a polymer is provided including a linker represented by Formula I:

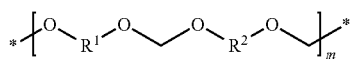

In Formula I, R$^1$ and R$^2$ are, independently, alkylene, alkenylene, arylene, heteroarylene, or alkylarylalkylene. In some embodiments, the polymer has a weight average molecular weight of about 500 g/mol to about 2,000,000 g/mol, and m is 1 to 1000. In some embodiments, R$^1$ is C$_2$-C$_{10}$ alkylene; and R$^2$ is a mixture of at least two of p-xylenyl, m-xylenyl, and o-xylenyl.

In another aspect a polymer is provided including a linker represented by Formula II:

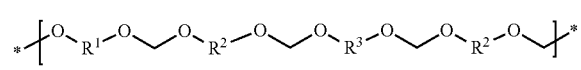

In Formula II, R$^1$, R$^2$, and R$^3$ are, independently, alkylene, alkenylene, arylene, heteroarylene, or alkylarylalkylene; and R$^1$ and R$^3$ are different. In some embodiments, the polymer has a weight average molecular weight of about 500 g/mol to about 2,000,000 g/mol. In some embodiments, R$^1$, R$^2$, or R$^3$ is a mixture of at least two of p-xylenyl, m-xylenyl, and o-xylenyl.

In another aspect a polymer is provided, the polymer represented by Formula III:

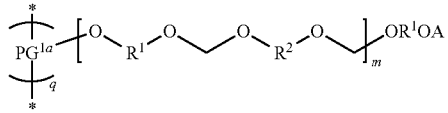

In Formula III, R$^1$ and R$^2$ are, independently, alkylene, alkenylene, arylene, heteroarylene, or alkylarylalkylene; A is hydrogen, alkyl, or —C(O)R$^4$; R$^4$ is hydrogen, alkyl, or phenyl; PG$^{1a}$ is the polymerization product of a polymerization group PG$^1$; and PG$^1$ is acrylyl, methacrylyl, isocycanyl, styrenyl, epoxyl, vinyl, oxetanyl, DL-lactidyl, or bicyclo[2.2.1]hept-2-enyl. In some embodiments, the polymer has a weight average molecular weight of about 500 g/mol to about 2,000,000 g/mol; m is 1 to 1000; and q is 1 to 1000. In some embodiments, R$^1$ is C$_2$-C$_{10}$ alkylene; and R$^2$ is a mixture of at least two of p-xylenyl, m-xylenyl, and o-xylenyl.

In another aspect a polymer is provided, where the polymer is represented by Formula IV:

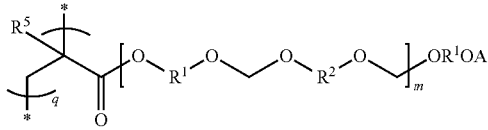

In Formula IV, R$^1$ and R$^2$ are, independently, alkylene, alkenylene, arylene, heteroarylene, or alkylarylalkylene; R$^5$ is hydrogen, CN, alkyl, or phenyl; A is hydrogen, alkyl, or —C(O)R$^4$; and R$^4$ is hydrogen, alkyl, or phenyl. In some embodiments, the polymer has a weight average molecular weight of about 500 g/mol to about 2,000,000 g/mol; m is 1 to 1000; and q is 1 to 1000. In some embodiments, R$^1$ is C$_2$-C$_{10}$ alkylene; and R$^2$ is a mixture of at least two of p-xylenyl, m-xylenyl, and o-xylenyl.

A method is provided for preparing polymer represented by Formula III. The method includes contacting XCH$_2$OR$^2$OCH$_2$X with HOR$^1$OH, HOR$^1$OA, and a base to form a polymer represented by Formula V

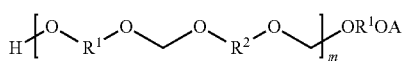

$$V$$

contacting the polymer represented by Formula V with a compound represented by PG$^1$-L and a base to form a polymer represented by Formula VI:

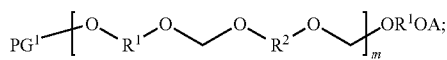

$$VI$$

and polymerizing PG$^1$ of the polymer represented by Formula VI to form the polymer represented by Formula III:

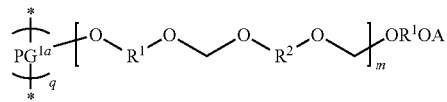

$$III$$

In Formulae III, V, and VI, R$^1$ and R$^2$ are, independently, alkylene, alkenylene, arylene, heteroarylene, or alkylarylalkylene; R$^4$ is hydrogen, alkyl, or phenyl; A is hydrogen, alkyl, or —C(O)R$^4$; X is a leaving group; PG$^1$ is a polymerizable group that is acrylyl, methacrylyl, isocycanyl, styrenyl, epoxyl, vinyl, oxetanyl, DL-lactidyl, or bicyclo[2.2.1]hept-2-enyl; PG$^{1a}$ is the polymerization product of the polymerizable group PG$^1$; L is a leaving group; m is 1 to 1000; and q is 1 to 1000. In some embodiments, R$^1$ is C$_2$-C$_{10}$ alkylene; and R$^2$ is a mixture of at least two of p-xylenyl, m-xylenyl, and o-xylenyl.

In another aspect, a method is provided for degrading a polymer, where the method includes providing a polymer including a linker represented by Formula I, contacting the polymer with acid; and obtaining a composition including HOR$^1$OH and HOR$^2$OH.

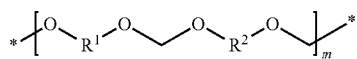

$$I$$

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has 1 to 16 carbon atoms, 1 to 12 carbons, 1 to 8 carbons or, in some embodiments, 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. In some embodiments, the alkyl groups may be substituted alkyl groups.

Heteroalkyl groups include alkyl groups, as defined herein, substituted by one or more O, N, or S atoms.

Cycloalkyl groups are cyclic alkyl groups having 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have 2 to 24 carbon atoms, and typically 2 to 10 carbons or, in some embodiments, 2 to 8, 2 to 6, or 2 to 4 carbon atoms. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

The terms "alkylene," "cycloalkylene," "alkenylene," "arylene," "heteroarylene," and "alkylarylalkylene" alone or as part of another substituent means a divalent radical derived from an alkyl, cycloalkyl, alkenyl, aryl, heteroaryl, or alkylarylalkyl group, respectively, as exemplified by —CH$_2$CH$_2$CH$_2$CH$_2$—. For alkylene, cycloalkylene, alkenylene, arylene, heteroarylene, and alkylarylalkylene linking groups, no orientation of the linking group is implied.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C (O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, heteroarylene, hetero moieties. Additionally, the substituents may be pendent from, or integral to, the carbon chain itself.

The present technology provides for polymers containing —OCH$_2$O— linker moieties that render the polymers chemically stable during commercial use but easily cleaved upon exposure to conditions (e.g., acidic conditions) not typically encountered during commercial use. The —OCH$_2$O— linker moieties can be combined with various monomers to tune the physical characteristics (e.g., flexibility, hardness, softness, etc.) of the polymer. The polymers described herein, having acid-sensitive —OCH$_2$O— linkers, are more readily degraded with acid and recycled than polymers made from conventional polymers e.g., those made from PET, polyethylene, or polypropylene. The polymers can be incorporated in packaging materials that can be readily degraded to monomeric starting materials following commercial use. Further, the monomeric starting materials that can readily be resynthesized (i.e., recycled) into the polymers described herein. Packaging made from the polymers described herein is cost effective, convenient, and light weight.

The polymers described herein can be used to make packaging, containers, and plastic goods for any application. For example, the polymers described herein can be used in wide variety of plastics for any application such as food, beverage, or consumer packaging, sport drink bottles, freeze vacuum containers, shipping cartons, bags, optical lenses, utensils, plates, toys, furniture coatings, automobile plastic components, fiberglass, cookware, plastic utensils, computers (e.g., tablets, laptops, netbooks) computer components, medical implants, mobile electronics, phones, calculators, paneling, coatings, fibers, insulation, seats, tables, shelves, table tops, counters, caulking and the like. The polymers described herein can also be used in aviation components.

As noted above, the polymers include a —OCH$_2$O— group. This group may be incorporated into a linker represented by Formula I:

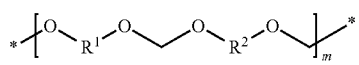

I

In Formula I, R$^1$ and R$^2$ are, independently, alkylene, alkenylene, arylene, heteroarylene, or alkylarylalkylene; the polymer has a weight average molecular weight of about 500 g/mol to about 2,000,000 g/mol, and m is 1 to 1000.

In Formula I, R$^1$ and R$^2$ are groups that are joined by the —OCH$_2$O— moieties. Each R$^1$ and R$^2$ group can be selected to tune the physical characteristics (e.g., flexibility, hardness, softness, etc.) of the polymer to accommodate the intended application (e.g., food packaging, consumer packaging, etc.) for the polymer. For example, flexible polymers generally include flexible alkyl groups at R$^1$ and/or R$^2$, whereas the polymer can be made more rigid by incorporating inflexible aryl groups at R$^1$ and/or R$^2$. Flexible groups impart "flexibility" and "softness" to the polymer, while rigid groups impart "rigidity" and "hardness." Such terms, while relative, are widely used in the art and are well-understood terms of distinction.

For example, R$^1$ may be alkylene in Formula I. In some embodiments, R$^1$ is C$_2$-C$_{10}$ alkylene. In some embodiments, R$^1$ is (CH$_2$)$_2$; (CH$_2$)$_4$; (CH$_2$)$_6$; or (CH$_2$)$_8$. In some embodiments, R$^1$ is (CH$_2$)$_4$. R$^1$ may be alkenylene. In some embodiments, R$^1$ is C$_2$-C$_{10}$ alkenylene. In some embodiments, R$^1$ is vinylene or allylene. R$^1$ may be arylene. In some embodiments, R$^1$ is phenylene, biphenylene, anthracenlyene, or naphthalenylene. R$^1$ may also be alkylarylalkylene. In some embodiments, R$^1$ is

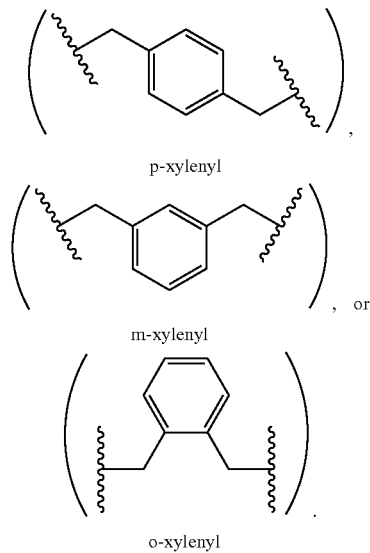

Further, R$^2$ may be alkylene in Formula I. In some embodiments, R$^2$ is C$_2$-C$_{10}$ alkylene. In some embodiments, R$^2$ is (CH$_2$)$_2$; (CH$_2$)$_4$; (CH$_2$)$_6$; or (CH$_2$)$_8$. In some embodiments, R$^2$ is (CH$_2$)$_4$. R$^2$ may be alkenylene. In some embodiments, R$^2$ is C$_2$-C$_{10}$ alkenylene. In some embodiments, R$^2$ is vinylene or allylene. R$^2$ may be arylene. In some embodiments, R$^2$ is phenylene, biphenylene, anthracenlyene, or naphthalenylene. R$^2$ may also be alkylarylalkylene. In some embodiments, R$^2$ is p-xylenyl, m-xylenyl, or o-xylenyl.

In Formula I, each R$^1$ and R$^2$ can independently be a mixture of groups. For example, each R$^1$ and R$^2$ can independently be a mixture of at least two of p-xylenyl, m-xylenyl, and o-xylenyl, where p-xylenyl groups, for example, can add rigidity to the polymer, whereas m-xylenyl groups, for example, can decrease the rigidity of the polymer.

In some embodiments, R$^1$ is C$_2$-C$_{10}$ alkylene; and R$^2$ is a mixture of at least two of p-xylenyl, m-xylenyl, and o-xylenyl. In some embodiments, R$^2$ is a mixture of p-xylenyl and m-xylenyl having a p-xylenyl:m-xylenyl ratio of about 2:1 to about 20:1. In some embodiments, $R^2$ is a mixture of p-xylenyl and m-xylenyl having a p-xylenyl:m-xylenyl ratio of about 5:1, 10:1, or 15:1. In some embodiments, $R^2$ is a mixture of p-xylenyl and o-xylenyl having a p-xylenyl:o-xylenyl ratio of about 2:1 to about 20:1. In some embodiments, $R^2$ is a mixture of p-xylenyl and o-xylenyl having a p-xylenyl:o-xylenyl ratio of about 5:1, 10:1, or 15:1.

The polymers of Formula I have a weight average molecular weight (Mw) of about 500 g/mol to about 2,000,000 g/mol. This may include an Mw of about 500 g/mol to about 500,000 g/mol, about 500 g/mol to about 100,000 g/mol, about 500 g/mol to about 50,000 g/mol, or about 500 g/mol to about 10,000 g/mol. Specific examples of Mw include about 500 g/mol, about 1,000 g/mol, about 5,000 g/mol, about 10,000 g/mol, about 20,000 g/mol, about 30,000 g/mol, about 40,000 g/mol, about 50,000 g/mol, about 60,000 g/mol, about 70,000 g/mol, about 80,000 g/mol, about 90,000 g/mol, about 100,000 g/mol, about 200,000 g/mol, about 250,000 g/mol, about 500,000 g/mol, about 750,000 g/mol, about 1,000,000 g/mol, about 2,000,000 g/mol, and ranges between any two of these values.

In some embodiments, m in Formula I is 1 to 1,000, 1 to 500, 1 to 250, 1 to 100, 1 to 50, or 1 to 10. Specific examples of m include 1, 2, 3, 4, 5, 6, 7, 8, 9, 10, 15, 20, 25, 30, 35, 40, 45, 50, 60, 70, 80 90, 100, 200, 250, 300, 400, 500, 750, 1,000, and ranges between any two of these values.

In accordance with another aspect a polymer is provided, where the polymer includes a linker represented by Formula II:

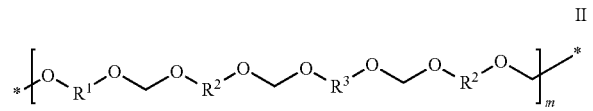

II

In Formula II, $R^1$, $R^2$, and $R^3$ are, independently, alkylene, alkenylene, arylene, heteroarylene, or alkylarylalkylene; $R^1$ and $R^3$ are different; the polymer has a weight average molecular weight of about 500 g/mol to about 2,000,000 g/mol, and m is 1 to 1000.

In Formula II, $R^1$ may be alkylene. In some embodiments, $R^1$ is $C_2$-$C_{10}$ alkylene. In some embodiments, $R^1$ is $(CH_2)_2$; $(CH_2)_4$; $(CH_2)_6$; or $(CH_2)_8$. In some embodiments, $R^1$ is $(CH_2)_4$. $R^1$ may be alkenylene. In some embodiments, $R^1$ is $C_2$-$C_{10}$ alkenylene. In some embodiments, $R^1$ is vinylene or allylene. $R^1$ may be arylene. In some embodiments, $R^1$ is phenylene, biphenylene, anthracenlyene, or naphthalenylene. $R^1$ may also be alkylarylalkylene. In some embodiments, $R^1$ is p-xylenyl, m-xylenyl, or o-xylenyl. $R^2$ may be alkylene in Formula II. In some embodiments, $R^2$ is $C_2$-$C_{10}$ alkylene. In some embodiments, $R^2$ is $(CH_2)_2$; $(CH_2)_4$; $(CH_2)_6$; or $(CH_2)_8$. In some embodiments, $R^2$ is $(CH_2)_4$. $R^2$ may be alkenylene. In some embodiments, $R^2$ is $C_2$-$C_{10}$ alkenylene. In some embodiments, $R^2$ is vinylene or allylene. $R^2$ may be arylene. In some embodiments, $R^2$ is phenylene, biphenylene, anthracenlyene, or naphthalenylene. $R^2$ may also be alkylarylalkylene. In some embodiments, $R^2$ is p-xylenyl, m-xylenyl, or o-xylenyl.

$R^3$ may be alkylene in Formula II. In some embodiments, $R^3$ is $C_2$-$C_{10}$ alkylene. In some embodiments, $R^3$ is $(CH_2)_2$; $(CH_2)_4$; $(CH_2)_6$; or $(CH_2)_8$. In some embodiments, $R^3$ is $(CH_2)_4$. $R^3$ may be alkenylene. In some embodiments, $R^3$ is $C_2$-$C_{10}$ alkenylene. In some embodiments, $R^3$ is vinylene or allylene. $R^3$ may be arylene. In some embodiments, $R^3$ is phenylene, biphenylene, anthracenlyene, or naphthalenylene. $R^3$ may also be alkylarylalkylene. In some embodiments, $R^3$ is p-xylenyl, m-xylenyl, or o-xylenyl. In some embodiments, $R^1$, $R^2$, or $R^3$ is a mixture of at least two of p-xylenyl, m-xylenyl, and o-xylenyl.

In some embodiments, the polymer has a weight average molecular weight (Mw) of about 500 g/mol to about 2,000,000, 500 g/mol to about 1,000,000 g/mol, about 500 g/mol to about 500,000 g/mol, about 500 g/mol to about 100,000 g/mol, about 500 g/mol to about 50,000 g/mol, or about 500 g/mol to about 10,000 g/mol. Specific examples of Mw include about 500 g/mol, about 1,000 g/mol, about 5,000 g/mol, about 10,000 g/mol, about 20,000 g/mol, about 30,000 g/mol, about 40,000 g/mol, about 50,000 g/mol, about 60,000 g/mol, about 70,000 g/mol, about 80,000 g/mol, about 90,000 g/mol, about 100,000 g/mol, about 200,000 g/mol, about 250,000 g/mol, about 500,000 g/mol, about 750,000 g/mol, about 1,000,000 g/mol, and ranges between any two of these values. In some embodiments, m is 1 to 500, 1 to 250, 1 to 100, 1 to 50, or 1 to 10. Specific examples of m include 1, 2, 3, 4, 5, 6, 7, 8, 9, 10, 15, 20, 25, 30, 35, 40, 45, 50, 60, 70, 80 90, 100, 200, 300, 400, 500, and ranges between any two of these values.

In some embodiments, $R^1$ and $R^3$ are alkylene; and $R^2$ is alkylarylalkylene. In some embodiments, $R^1$ and $R^3$ are alkylarylalkylene; and $R^2$ is alkylene. In some embodiments, each alkylarylalkylene is a mixture of at least two of p-xylenyl, m-xylenyl, and o-xylenyl.

In some embodiments, each alkylarylalkylene is, independently, a mixture of p-xylenyl and m-xylenyl having a p-xylenyl:m-xylenyl ratio of about 2:1 to about 20:1. In some embodiments, each alkylarylalkylene is, independently, a mixture of p-xylenyl and o-xylenyl having a p-xylenyl:o-xylenyl ratio of about 2:1 to about 20:1. In some embodiments, each alkylene is $C_1$-$C_{10}$ alkylene. In some embodiments, each alkylene is $(CH_2)_2$; $(CH_2)_4$; $(CH_2)_6$; or $(CH_2)_8$.

The linkers described above may be the entire, stand-alone polymer, or the linker may be incorporated into other polymers. For example, the polymer may be represented by Formula III:

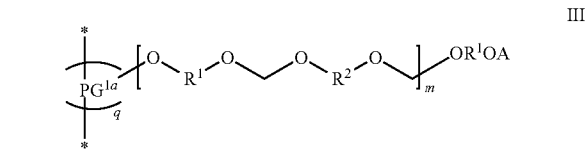

III

In Formula III, $R^1$ and $R^2$ are, independently, alkylene, alkenylene, arylene, heteroarylene, or alkylarylalkylene; A is hydrogen, alkyl, or —C(O)$R^4$; $R^4$ is hydrogen, alkyl, or phenyl; $PG^{1a}$ is the polymerization product of a polymerization group $PG^1$; $PG^1$ is acrylyl, methacrylyl, isocycanyl, styrenyl, epoxyl, vinyl, oxetanyl, DL-lactidyl, or bicyclo[2.2.1]hept-2-enyl; the polymer has a weight average molecular weight of about 500 g/mol to about 2,000,000 g/mol; m is 1 to 1000; and q is 1 to 1000.

In Formula III, $R^1$ may be alkylene. In some embodiments, $R^1$ is $C_2$-$C_{10}$ alkylene. In some embodiments, $R^1$ is $(CH_2)_2$; $(CH_2)_4$; $(CH_2)_6$; or $(CH_2)_8$. In some embodiments, $R^1$ is $(CH_2)_4$. $R^1$ may be alkenylene. In some embodiments, $R^1$ is $C_2$-$C_{10}$ alkenylene. In some embodiments, $R^1$ is vinylene or allylene. $R^1$ may be arylene. In some embodiments, $R^1$ is phenylene, biphenylene, anthracenlyene, or naphthalenylene.

$R^1$ may also be alkylarylalkylene. In some embodiments, $R^1$ is p-xylenyl, m-xylenyl, or o-xylenyl.

$R^2$ may be alkylene in Formula III. In some embodiments, $R^2$ is $C_2$-$C_{10}$ alkylene. In some embodiments, $R^2$ is $(CH_2)_2$; $(CH_2)_4$; $(CH_2)_6$; or $(CH_2)_8$. In some embodiments, $R^2$ is $(CH_2)_4$. $R^2$ may be alkenylene. In some embodiments, $R^2$ is $C_2$-$C_{10}$ alkenylene. In some embodiments, $R^2$ is vinylene or allylene. $R^2$ may be arylene. In some embodiments, $R^2$ is phenylene, biphenylene, anthracenlyene, or naphthalenylene. $R^2$ may also be alkylarylalkylene. In some embodiments, $R^2$ is p-xylenyl, m-xylenyl, or o-xylenyl.

In some embodiments, the polymer has a Mw of about 500 g/mol to about 1,000,000. This may include an Mw of about 500 g/mol to about 500,000, about 500 g/mol to about 100,000, about 500 g/mol to about 50,000, or about 500 g/mol to about 10,000. Specific examples of Mw include about 500 g/mol, about 1,000 g/mol, about 5,000 g/mol, about 10,000 g/mol, about 20,000 g/mol, about 30,000 g/mol, about 40,000 g/mol, about 50,000 g/mol, about 60,000 g/mol, about 70,000 g/mol, about 80,000 g/mol, about 90,000 g/mol, about 100,000 g/mol, about 200,000 g/mol, about 250,000 g/mol, about 500,000 g/mol, about 750,000 g/mol, about 1,000,000 g/mol, about 2,000,000, and ranges between any two of these values. In some embodiments, m is 1 to 500, 1 to 250, 1 to 100, 1 to 50, or 1 to 10. Specific examples of m include 1, 2, 3, 4, 5, 6, 7, 8, 9, 10, 15, 20, 25, 30, 35, 40, 45, 50, 60, 70, 80 90, 100, 200, 250, 300, 400, 500, 750, 1,000,000, and ranges between any two of these values. Specific examples of q include 1, 2, 3, 4, 5, 6, 7, 8, 9, 10, 15, 20, 25, 30, 35, 40, 45, 50, 100, 200, 300, 400, 500, 600, 700, 800, 900, 1,000, and ranges between any two of these values.

In accordance with another aspect a polymer is provided, where the polymer is represented by Formula IV:

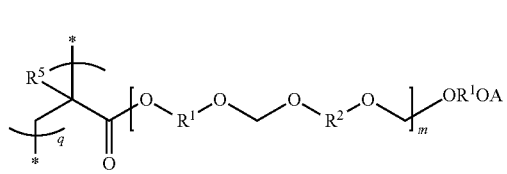

IV

In Formula IV, $R^1$ and $R^2$ are, independently, alkylene, alkenylene, arylene, heteroarylene, or alkylarylalkylene; $R^5$ is hydrogen, CN, alkyl, or phenyl; A is hydrogen, alkyl, or —C(O)$R^4$; $R^4$ is hydrogen, alkyl, or phenyl; the polymer has a weight average molecular weight of about 500 g/mol to about 2,000,000 g/mol; m is 1 to 1000; and q is 1 to 1000.

In Formula IV, $R^1$ may be alkylene. In some embodiments, $R^1$ is $C_2$-$C_{10}$ alkylene. In some embodiments, $R^1$ is $(CH_2)_2$; $(CH_2)_4$; $(CH_2)_6$; or $(CH_2)_8$. In some embodiments, $R^1$ is $(CH_2)_4$. $R^1$ may be alkenylene. In some embodiments, $R^1$ is $C_2$-$C_{10}$ alkenylene. In some embodiments, $R^1$ is vinylene or allylene. $R^1$ may be arylene. In some embodiments, $R^1$ is phenylene, biphenylene, anthracenlyene, or naphthalenylene. $R^1$ may also be alkylarylalkylene. In some embodiments, $R^1$ is p-xylenyl, m-xylenyl, or o-xylenyl.

$R^2$ may be alkylene in Formula IV. In some embodiments, $R^2$ is $C_2$-$C_{10}$ alkylene. In some embodiments, $R^2$ is $(CH_2)_2$; $(CH_2)_4$; $(CH_2)_6$; or $(CH_2)_8$. In some embodiments, $R^2$ is $(CH_2)_4$. $R^2$ may be alkenylene. In some embodiments, $R^2$ is $C_2$-$C_{10}$ alkenylene. In some embodiments, $R^2$ is vinylene or allylene. $R^2$ may be arylene. In some embodiments, $R^2$ is phenylene, biphenylene, anthracenlyene, or naphthalenylene. $R^2$ may also be alkylarylalkylene. In some embodiments, $R^2$ is p-xylenyl, m-xylenyl, or o-xylenyl.

In some embodiments, the polymer has a weight average molecular weight (Mw) of about 500 g/mol to about 2,000,000, about 500 g/mol to about 1,000,000, about 500 g/mol to about 500,000, about 500 g/mol to about 100,000, about 500 g/mol to about 50,000, or about 500 g/mol to about 10,000. Specific examples of Mw include about 500 g/mol, about 1,000 g/mol, about 5,000 g/mol, about 10,000 g/mol, about 20,000 g/mol, about 30,000 g/mol, about 40,000 g/mol, about 50,000 g/mol, about 60,000 g/mol, about 70,000 g/mol, about 80,000 g/mol, about 90,000 g/mol, about 100,000 g/mol, about 200,000 g/mol, about 250,000 g/mol, about 500,000 g/mol, about 750,000 g/mol, about 1,000,000 g/mol, about 2,000,000, and ranges between any two of these values. In some embodiments, m is 1 to 50. In some embodiments, m is 1 to 40, 1 to 30, 1 to 20, 1 to 10, 1 to 5. Specific examples of m include 1, 2, 3, 4, 5, 6, 7, 8, 9, 10, 15, 20, 25, 30, 35, 40, 45, 50, 60, 70, 80 90, 100, 200, 250, 300, 400, 500, 750, 1,000,000, and ranges between any two of these values. In some embodiments, q is 1 to 50. In some embodiments, q is 1 to 40, 1 to 30, 1 to 20, 1 to 10, or 1 to 5. Specific examples of q include 1, 2, 3, 4, 5, 6, 7, 8, 9, 10, 15, 20, 25, 30, 35, 40, 45, 50, 100, 200, 300, 400, 500, 600, 700, 800, 900, 1,000, and ranges between any two of these values.

In some embodiments, $R^1$ is $(CH_2)_2$; $(CH_2)_4$; $(CH_2)_6$; or $(CH_2)_8$; and $R^2$ is a mixture of at least two of p-xylenyl, m-xylenyl, and o-xylenyl.

The above polymers are amenable to forming into a wide variety of articles as introduced above. The polymers may be formed into articles using techniques such as blowing, compaction molding, compression molding, injection molding, extrusion, rotomolding, vacuum molding, thermoforming, and the like as are known in the art.

In accordance with another aspect a method is provided of preparing polymer represented by Formula III where the method includes: contacting $XCH_2OR^2OCH_2X$ with $HOR^1OH$, $HOR^1OA$, and a base to form a polymer represented by Formula V

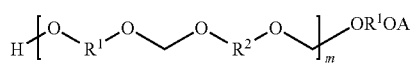

V contacting the polymer represented by Formula V with a compound represented by $PG^1$-L and a base to form a polymer represented by Formula VI:

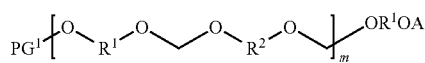

VI and polymerizing $PG^1$ of the polymer represented by Formula VI to form the polymer represented by Formula III:

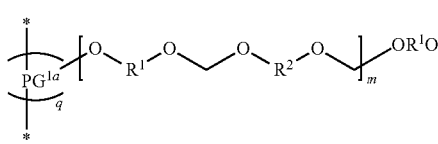

III

In Formulae III, V, and VI, $R^1$ and $R^2$ are, independently, alkylene, alkenylene, arylene, heteroarylene, or alkylarylalkylene; A is hydrogen, alkyl, or $C(O)R^4$; $R^4$ is hydrogen, alkyl, or phenyl; X is a leaving group; $PG^1$ is a polymerizable group selected from the group consisting of acrylyl, methacrylyl, isocycanyl, styrenyl, epoxyl, vinyl, oxetanyl, DL-lactidyl, and bicyclo[2.2.1]hept-2-enyl; $PG^{1a}$ is the polymerization product of the polymerizable group $PG^1$; L is a leaving group; m is 1 to 1000; and q is 1 to 1000.

In Formula III, $R^1$ may be alkylene. In some embodiments, $R^1$ is $C_2-C_{10}$ alkylene. In some embodiments, $R^1$ is $(CH_2)_2$; $(CH_2)_4$; $(CH_2)_6$; or $(CH_2)_8$. In some embodiments, $R^1$ is $(CH_2)_4$. $R^1$ may be alkenylene. In some embodiments, $R^1$ is $C_2-C_{10}$ alkenylene. In some embodiments, $R^1$ is vinylene or allylene. $R^1$ may be arylene. In some embodiments, $R^1$ is phenylene, biphenylene, anthracenlyene, or naphthalenylene. $R^1$ may also be alkylarylalkylene. In some embodiments, $R^1$ is p-xylenyl, m-xylenyl, or o-xylenyl.

$R^2$ may be alkylene in Formula III. In some embodiments, $R^2$ is $C_2-C_{10}$ alkylene. In some embodiments, $R^2$ is $(CH_2)_2$; $(CH_2)_4$; $(CH_2)_6$; or $(CH_2)_8$. In some embodiments, $R^2$ is $(CH_2)_4$. $R^2$ may be alkenylene. In some embodiments, $R^2$ is $C_2-C_{10}$ alkenylene. In some embodiments, $R^2$ is vinylene or allylene. $R^2$ may be arylene. In some embodiments, $R^2$ is phenylene, biphenylene, anthracenlyene, or naphthalenylene. $R^2$ may also be alkylarylalkylene. In some embodiments, $R^2$ is p-xylenyl, m-xylenyl, or o-xylenyl.

In some embodiments, the polymer has a weight average molecular weight (Mw) of about 500 g/mol to about 2,000,000 g/mol, about 500 g/mol to about 1,000,000 g/mol, about 500 g/mol to about 500,000 g/mol, about 500 g/mol to about 100,000 g/mol, about 500 g/mol to about 50,000 g/mol, or about 500 g/mol to about 10,000 g/mol. Specific examples of Mw include about 500 g/mol, about 1,000 g/mol, about 5,000 g/mol, about 10,000 g/mol, about 20,000 g/mol, about 30,000 g/mol, about 40,000 g/mol, about 50,000 g/mol, about 60,000 g/mol, about 70,000 g/mol, about 80,000 g/mol, about 90,000 g/mol, about 100,000 g/mol, about 200,000 g/mol, about 250,000 g/mol, about 500,000 g/mol, about 750,000 g/mol, about 1,000,000 g/mol, about 2,000,000, and ranges between any two of these values.

In some embodiments, the polymer represented by Formula III is a polymer represented by Formula IV:

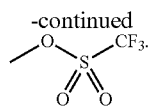

In Formula IV, $R^5$ is hydrogen, CN, alkyl, or phenyl.

In some embodiments, the method further includes forming $XCH_2OR^2OCH_2X$ by contacting $R^6OCH_2OR^2OCH_2OR^6$ with HX, where $R^6$ is alkyl. In some embodiments, $R^6$ is methyl, ethyl, propyl, butyl, pentyl, hexyl, heptyl, or octyl In some embodiments, X is Cl, Br, I,

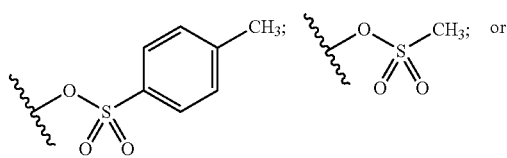

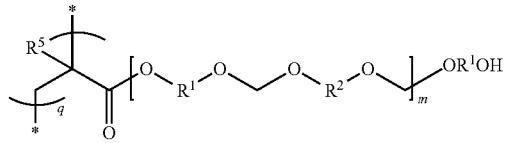

In some embodiments, L is Cl, Br, I,

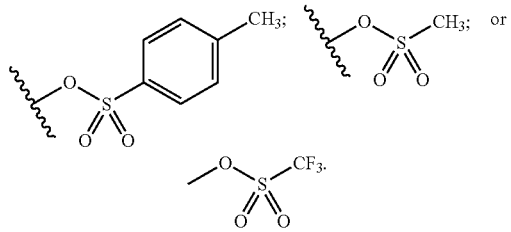

In some embodiments, X and L are both Cl.

In some embodiments, the base is a tertiary amine, secondary amine, pyridine, or a carbonate salt. In some embodiments, the base is morpholine, N-methylmorpholine, piperidine, N-methylpiperidine, piperazine, N-methylpiperazine, N,N-dimethylpiperazine, triethylamine, diisopropylethylamine, or pyridine.

In another aspect, a method is provided for degrading any of the above polymers, the method including providing the polymer, contacting the polymer with acid, and obtaining a composition including alcohol degradation products. For example, where the polymer is that of Formula I, above, the alcohol degradation products will include $HOR^1OH$ and $HOR^2OH$. Where the polymer includes a further polymeric moiety or polymerizable group, such as those represented in Formulas III, IV, and VI, the degradation products will include the polymer fragments as well as the alcohol degradation products.

Because the polymers described above are originally prepared from alcohols such as $HOR^1OH$ and $HOR^2OH$, the acid degradation provides again the starting materials for the polymerization. Thus, at least in the segments of the polymer which include $R^1$ and $R^2$ the regeneration of the starting materials is realized. These materials may then be used to make other polymers. Because the polymers are degraded into their original starting materials, the above polymers provide at least one advantage over other recycled plastics and polymers, that advantage being that the recycled (actually re-polymerized) polymers are the same as the original polymers. Other recycled plastics typically grinder the polymers into smaller fragments, then treat the terminal groups to link together the smaller fragments and oligomers. The present "recycled" polymers are to be completely reconstructed from the original starting materials that are recovered from the degradation process.

Illustrative acids for use in the methods of degrading include, but are not limited to, HCl, HBr, $H_2SO_4$, acetic acid, trifluoroacetic acid, phosphoric acid, nitric acid, and combinations thereof. The acid may be added as the neat acid to the polymer or as a diluted solution such as an aqueous solution. Such an aqueous acid solution can have any pH of less than 7.0. Representative pH values for the acidic solution that is added to the polymer may be <6.0, <5.0, <4.0, <3.0, <2.0, or <1.0.

The temperature of the degradation will impact the rate at which the degradation occurs. Accordingly, a wide range of temperatures may be employed. For example, the contacting may be conducted at a temperature of about 20° C. to about 200° C. This will include temperatures of about 20° C. to about 150° C., or about 20° C. to about 100° C., or about 20° C. to about 50° C. In some embodiments, the contacting is conducted at room temperature.

The present technology, thus generally described, will be understood more readily by reference to the following Examples, which are provided by way of illustration and are not intended to be limiting of the present technology.

EXAMPLES

Example 1

Synthesis of Representative Polymers

Polymer 1.1:

Butane-1,4-diol (1 mmol) and 1,4-bis(chloromethoxy)butane (1 mmol) are combined in DMF (10 mL) with piperidine (2.5 mmol) and stirred 1 hour at 60° C. Polymer 1.1 precipitates from solution and is washed with dilute aqueous HCl (0.1M), aqueous $NaHCO_3$, and water. Polymer 1.1 is expected to be softer and more flexible than polymers 1.2 and 1.3, described below. The softness, hardness, and flexibility of these polymers can be measured according to protocols known in the art, such as ASTM D4145-10 *Standard Test Method for Coating Flexibility of Prepainted Sheet*, ASTM D1004-09 *Standard Test Method for Tear Resistance (Graves Tear) of Plastic Film and Sheeting*, and ASTM D3892-93 (2009) *Standard Practice for Packaging/Packing of Plastics*.

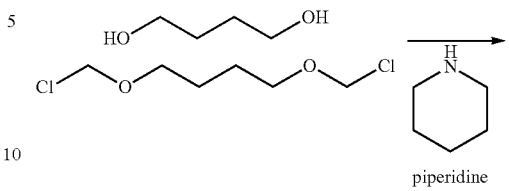

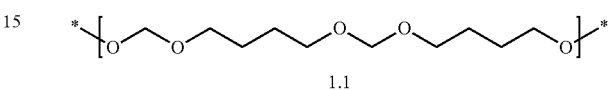

Polymer 1.2:

Ethane-1,2-diol (1 mmol) and 1,4-bis((chloromethoxy)methyl) benzene (1 mmol) are combined in DMF (10 mL) with piperidine (2.5 mmol) and stirred 1 hour at 60° C. Polymer 1.2 precipitates from solution and is washed with dilute aqueous HCl (0.1M), aqueous $NaHCO_3$, and water. Polymer 1.2 is expected to be harder and more rigid than polymers 1.1 and 1.3.

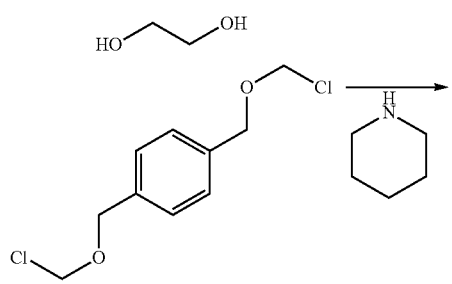

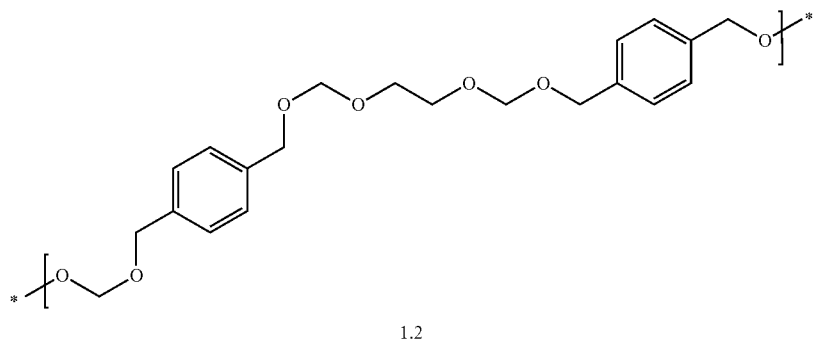

Polymer 1.3:

Ethane-1,2-diol (1 mmol), 1,3-bis((chloromethoxy)methyl)benzene (0.1 mmol), and 1,4-bis((chloromethoxy)methyl)benzene (1 mmol) are combined in DMF (10 mL) with piperidine (2.5 mmol) and stirred 1 hour at 60° C. Polymer 1.3 precipitates from solution and is washed with dilute aqueous HCl (0.1M), aqueous NaHCO$_3$, and water. Polymer 1.3 is expected to be harder and more rigid than polymers 1.1 but softer and more flexible than polymer 1.2.

Synthetic methods substantially similar to those shown above can be used to make any of the polymers described herein.

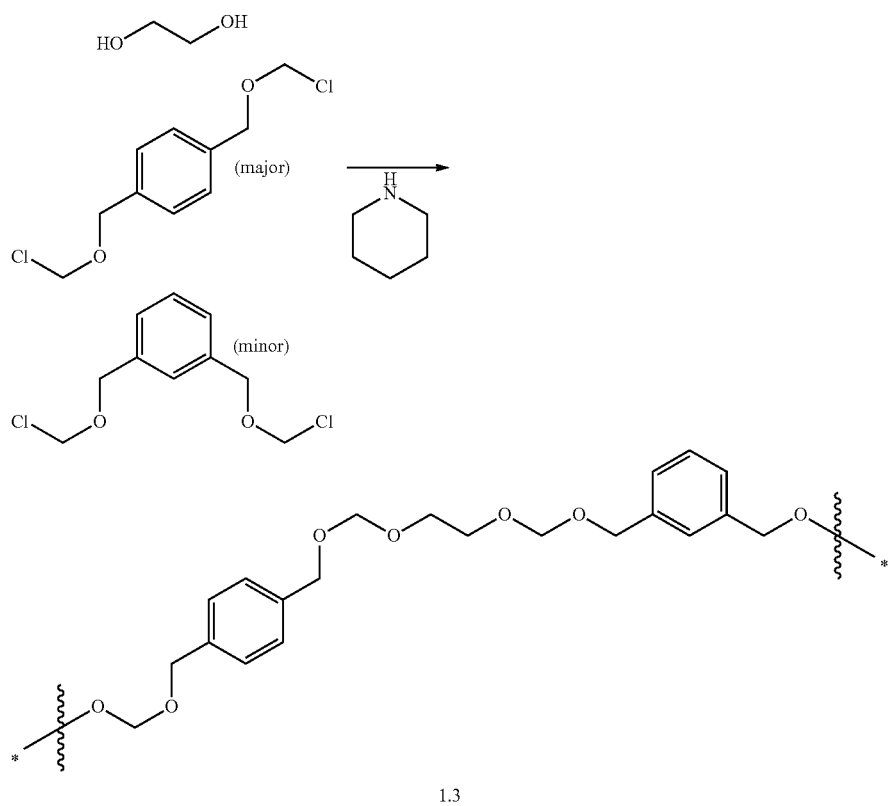

Example 2

Degradation of Representative Polymers

Polymer 1.1 is treated with CH$_2$Cl$_2$ and gaseous HCl and stirred 3 hours. The reaction mixture is concentrated and the crude butane-1,4-diol can be used directly in example 3 without further treatment or purification.

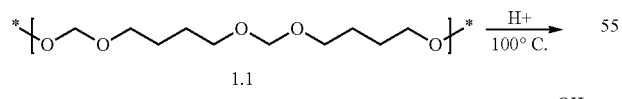

Example 3

Recycling of Representative Polymers

Polymer 1.1 is "recycled" by bubbling HCl gas into a mixture of crude butane-1,4-diol (1 mmol) and formaldehyde (2.5 mmol). The crude 1,4-bis(chloromethoxy)butane can be modified as shown in Example 1 to yield polymer 1.1.

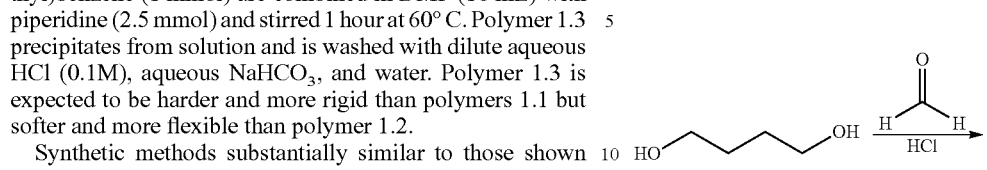

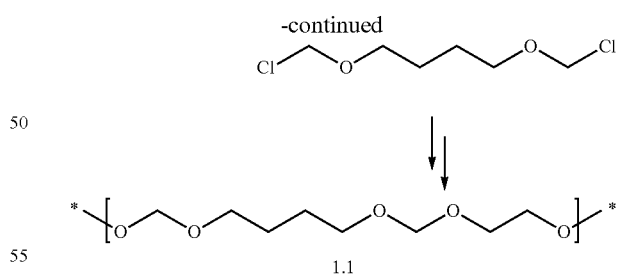

The polymers described herein, such as those of Examples 1 and 2, have acid-sensitive —OCH$_2$O— linkers, are more readily degraded with acid than conventional polymers e.g., those made from PET, polyethylene, or polypropylene. The polymers described herein, such as those of Example 3, are also more easily recycled than conventional polymers.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A polymer comprising a linker represented by Formula II:

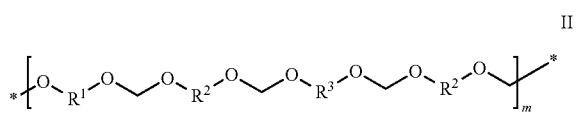

wherein:
$R^1$, $R^2$, and $R^3$ are, independently, alkylene, alkenylene, arylene, heteroarylene, or alkylarylalkylene;
$R^1$ and $R^3$ are different;
the polymer has a weight average molecular weight of about 500 g/mol to about 2,000,000 g/mol; and
m is 1 to 1000.

2. The polymer of claim 1, wherein:
$R^1$ and $R^3$ are alkylene; and
$R^2$ is alkylarylalkylene.

3. The polymer of claim 1, wherein:
$R^1$ and $R^3$ are alkylarylalkylene; and
$R^2$ is alkylene.

4. The polymer of claim 1, wherein each alkylarylalkylene is a mixture of at least two of p-xylenyl, m-xylenyl, and o-xylenyl.

5. The polymer of claim 1, wherein each alkylarylalkylene is, independently, a mixture of p-xylenyl and m-xylenyl having a p-xylenyl:m-xylenyl ratio of about 2:1 to about 20:1.

6. The polymer of claim 1, wherein each alkylarylalkylene is, independently, a mixture of p-xylenyl and o-xylenyl having a p-xylenyl:o-xylenyl ratio of about 2:1 to about 20:1.

7. The polymer of claim 1, wherein each alkylene is $C_1$-$C_{10}$ alkylene.

8. The polymer of claim 7, wherein each alkylene is $(CH_2)_2$; $(CH_2)_4$; $(CH_2)_6$; or $(CH_2)_8$.

9. The polymer of claim 1, wherein m is 1 to 50.

10. A polymer represented by Formula IV:

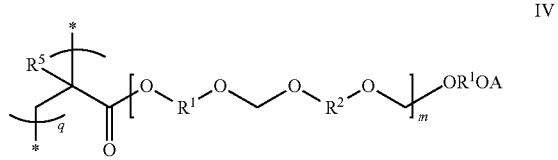

wherein:
A is hydrogen, alkyl, or $—C(O)R^4$;
$R^1$ and $R^2$ are, independently, alkylene, alkenylene, arylene, heteroarylene, or alkylarylalkylene;
$R^4$ is hydrogen, alkyl, or phenyl;
$R^5$ is hydrogen, CN, alkyl, or phenyl;
the polymer has a weight average molecular weight of about 500 g/mol to about 2,000,000 g/mol;
m is 1 to 1000; and
q is 1 to 1000.

11. The polymer of claim 10, wherein:
$R^1$ is $(CH_2)_2$; $(CH_2)_4$; $(CH_2)_6$; or $(CH_2)_8$; and
$R^2$ is a mixture of at least two of p-xylenyl, m-xylenyl, and o-xylenyl.

12. The polymer of claim 10, wherein m is 1 to 50.

13. The polymer of claim 10, wherein q is 1 to 50.

14. A method of degrading a polymer, the method comprising:
provide a polymer comprising a linker represented by Formula I:
contacting the polymer with an acid; and
obtaining a composition including $HOR^1OH$ and $HOR^2OH$;
wherein:

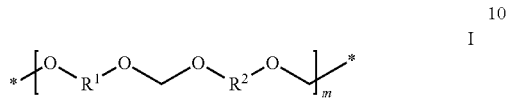

I $R^1$ and $R^2$ are, independently, alkylene, alkenylene, arylene, heteroarylene, or alkylarylalkylene; and
m is 1 to 1000.

15. The method of claim 14, further comprising converting the composition including $HOR^1OH$ and $HOR^2OH$ to a recycled polymer comprising the linker represented by Formula I.

16. The method of claim 14, wherein the acid is selected from the group consisting of HCl, HBr, $H_2SO_4$, acetic acid, trifluoroacetic acid, phosphoric acid, and nitric acid.

17. The method of claim 14, wherein the contacting further comprises contacting at a temperature of from about 20° C. to about 120° C.

18. The method of claim 14, wherein the providing the polymer includes the linker having a value of m from about 1 to about 50, inclusive.

* * * * *

UNITED STATES PATENT AND TRADEMARK OFFICE
CERTIFICATE OF CORRECTION

Page 1 of 2

PATENT NO. : 8,952,102 B2
APPLICATION NO. : 14/297990
DATED : February 10, 2015
INVENTOR(S) : Carlson et al.

It is certified that error appears in the above-identified patent and that said Letters Patent is hereby corrected as shown below:

On the title page, below item (63), insert item -- (30) Foreign Application Priority Data
July 31, 2012 (WO)................ PCT/US2012/048980 --.

In the Specification

In Column 1, Lines 7-8, delete "This application is a continuation of U.S. patent application Ser. No. 13/761,512, filed on Feb. 7, 2013," and insert -- This application is a continuation under 35 U.S.C. §120 of U.S. patent application Ser. No. 13/761,512, filed on Feb. 7, 2013, now Pat. No. 8,779,070, --, therefor.

In Column 2, Line 67, delete "Formula V" and insert -- Formula V: --, therefor.

In Column 7, Line 26, delete "80 90," and insert -- 80, 90, --, therefor.

In Column 7, Lines 52-61, delete "$R^2$ may be.....................or o-xylenyl." and insert the same at Line 53, as a new Paragraph.

In Column 8, Line 22, delete "80 90," and insert -- 80, 90, --, therefor.

In Column 9, Line 12, delete "a Mw" and insert -- an Mw --, therefor.

In Column 9, Line 27, delete "80 90," and insert -- 80, 90, --, therefor.

In Column 10, Line 20, delete "80 90," and insert -- 80, 90, --, therefor.

In Column 10, Line 40, delete "Formula V" and insert -- Formula V: --, therefor.

In Column 11, Line 3, delete "C(O)$R^4$;" and insert -- -C(O)$R^4$; --, therefor.

Signed and Sealed this
Fourth Day of August, 2015

Michelle K. Lee
*Director of the United States Patent and Trademark Office*

CERTIFICATE OF CORRECTION (continued)
U.S. Pat. No. 8,952,102 B2

In Column 11, Line 57, delete "octyl" and insert -- octyl. --, therefor.

In Column 12, Line 32, delete "HOR'OH" and insert -- HOR$^1$OH --, therefor.